United States Patent
Fetzer et al.

(10) Patent No.: US 9,664,652 B2
(45) Date of Patent: May 30, 2017

(54) NON-DESTRUCTIVE ULTRASONIC INSPECTION APPARATUS, SYSTEMS, AND METHODS

(71) Applicant: The Boeing Company, Chicago, IL (US)

(72) Inventors: Barry A. Fetzer, Renton, WA (US); Christopher R. Brown, Seattle, WA (US); Kevin R. Bray, Seattle, WA (US); Michael J. Duncan, Lake Tapps, WA (US); Steven R. Walton, Cottonwood, ID (US)

(73) Assignee: The Boeing Company, Chicago, IL (US)

( * ) Notice: Subject to any disclaimer, the term of this patent is extended or adjusted under 35 U.S.C. 154(b) by 190 days.

(21) Appl. No.: 14/528,897

(22) Filed: Oct. 30, 2014

(65) Prior Publication Data
US 2016/0123933 A1    May 5, 2016

(51) Int. Cl.
G01N 9/24       (2006.01)
G01N 29/265     (2006.01)
(Continued)

(52) U.S. Cl.
CPC ......... *G01N 29/265* (2013.01); *G01N 29/225* (2013.01); *G01N 29/24* (2013.01);
(Continued)

(58) Field of Classification Search
CPC ........... G01N 29/24; G01N 2291/2694; G01N 29/225
See application file for complete search history.

(56) References Cited

U.S. PATENT DOCUMENTS 4,472,975 A * 9/1984 Beck ...................... G01N 29/28
                                                    73/622
5,469,744 A * 11/1995 Patton .................. G10K 11/004
                                                    73/644
(Continued)

FOREIGN PATENT DOCUMENTS

DE       3719105      12/1988
EP       1625676       4/2013
(Continued)

OTHER PUBLICATIONS

Sanz, et al., Robotized Inspection System of the External Aircraft Fuselage based on Ultrasound, The 2010 IEEE/RSJ International Conference on Intelligent Robots and Systems, Oct. 18-22, 2010, Taipei, Taiwan.
(Continued)

*Primary Examiner* — Harshad R Patel
*Assistant Examiner* — Samir M Shah
(74) *Attorney, Agent, or Firm* — Kunzler Law Group, PC

(57) ABSTRACT

As described herein, a system for inspecting a component includes an ultrasonic inspection probe with a component surface interface, and a robotic device with an end effector coupled to the ultrasonic inspection probe. The robotic device is automatably controllable to move the ultrasonic inspection probe across a surface of the component. Additionally, the system includes an angle sensor subsystem coupled between the ultrasonic inspection probe and the end effector. The angle sensor subsystem is configured to operably detect an actual orientation of the end effector relative to a presently inspected portion of the surface of the component. The system includes a controller configured to receive orientation data from the angle sensor subsystem, the orientation data comprising the actual orientation of the end effector, compare the actual orientation to a desired orientation, and control the robotic device to adjust an (Continued)

orientation of the end effector to be in the desired orientation.

19 Claims, 9 Drawing Sheets

(51) Int. Cl.
*G01N 29/24* (2006.01)
*G01N 29/28* (2006.01)
*G01N 29/22* (2006.01)

(52) U.S. Cl.
CPC ....... *G01N 29/28* (2013.01); *G01N 2291/106* (2013.01); *G01N 2291/2694* (2013.01)

(56) References Cited

U.S. PATENT DOCUMENTS

| | | | |
|---|---|---|---|
| 5,814,731 A * | 9/1998 | Alexander | G01N 29/225 |
| | | | 73/624 |
| 5,984,415 A | 11/1999 | Schumacher et al. | |
| 5,986,762 A | 11/1999 | Challener | |
| 6,344,656 B1 | 2/2002 | Hopkins | |
| 6,481,290 B1 * | 11/2002 | MacInnis | G01N 29/11 |
| | | | 73/644 |
| 6,658,939 B2 | 12/2003 | Georgeson et al. | |
| 6,733,457 B2 * | 5/2004 | Flesch | A61B 8/12 |
| | | | 600/459 |
| 6,948,369 B2 * | 9/2005 | Fleming | G01N 3/00 |
| | | | 228/104 |
| 7,034,271 B1 | 4/2006 | Sinclair | |
| 7,249,512 B2 | 7/2007 | Kennedy et al. | |
| 7,263,889 B2 | 9/2007 | Kennedy et al. | |
| 7,617,732 B2 | 11/2009 | Bui et al. | |
| 7,640,810 B2 | 1/2010 | Kennedy et al. | |
| 7,640,811 B2 | 1/2010 | Kennedy et al. | |
| 7,643,893 B2 | 1/2010 | Troy et al. | |
| 7,644,618 B2 | 1/2010 | Fetzer et al. | |
| 7,690,259 B2 | 4/2010 | Bui et al. | |
| 7,743,660 B2 | 6/2010 | Marsh et al. | |
| 7,784,348 B2 | 8/2010 | Dubois et al. | |
| 7,836,768 B2 | 11/2010 | Young et al. | |
| 7,859,655 B2 | 12/2010 | Troy et al. | |
| 8,082,793 B2 | 12/2011 | Sarr et al. | |
| 8,087,298 B1 * | 1/2012 | DiMambro | G01N 29/226 |
| | | | 73/629 |
| 8,128,027 B2 | 3/2012 | Lee | |
| 8,438,928 B2 * | 5/2013 | Frederick | G01N 29/07 |
| | | | 73/627 |
| 8,459,120 B2 * | 6/2013 | Keeton | G01N 29/223 |
| | | | 73/618 |
| 8,650,959 B2 * | 2/2014 | De Odorico | G01N 29/225 |
| | | | 73/644 |
| 8,892,252 B1 | 11/2014 | Troy et al. | |
| 9,126,676 B2 * | 9/2015 | DeCraene | B64C 13/04 |
| 9,127,971 B2 | 9/2015 | Sarr | |
| 9,316,619 B2 * | 4/2016 | Lombardo | G01N 27/902 |
| 9,354,206 B2 * | 5/2016 | Zalameda | G01N 29/045 |
| 9,372,173 B2 * | 6/2016 | Thomson | G01N 29/221 |
| 2006/0243051 A1 | 11/2006 | Bui | |
| 2010/0224001 A1 * | 9/2010 | Brignac | G01N 29/07 |
| | | | 73/639 |
| 2012/0025031 A1 * | 2/2012 | Stachniak | B64C 13/12 |
| | | | 244/223 |
| 2012/0097800 A1 * | 4/2012 | Burroughs | B64C 13/12 |
| | | | 244/197 |
| 2012/0160967 A1 * | 6/2012 | Scott | B64C 13/02 |
| | | | 244/223 |
| 2013/0105634 A1 * | 5/2013 | DeCraene | B64C 13/04 |
| | | | 244/223 |
| 2013/0145850 A1 | 6/2013 | Lute, Jr. et al. | |
| 2013/0209256 A1 * | 8/2013 | Yates | F01D 7/00 |
| | | | 416/112 |
| 2014/0305216 A1 * | 10/2014 | Hafenrichter | G01N 29/07 |
| | | | 73/598 |
| 2014/0373608 A1 | 12/2014 | Bellemare | |
| 2014/0376768 A1 | 12/2014 | Troy et al. | |
| 2015/0053015 A1 | 2/2015 | Sarr et al. | |
| 2015/0329221 A1 | 11/2015 | Georgeson et al. | |
| 2016/0123934 A1 | 5/2016 | Fetzer et al. | |

FOREIGN PATENT DOCUMENTS

| | | |
|---|---|---|
| JP | 2013088242 A | 5/2013 |
| WO | 2005/032003 | 4/2005 |
| WO | 2013/070840 | 5/2013 |

OTHER PUBLICATIONS

European Search Report for EP Application No. 15192433.9 dated Apr. 14, 2016.

* cited by examiner

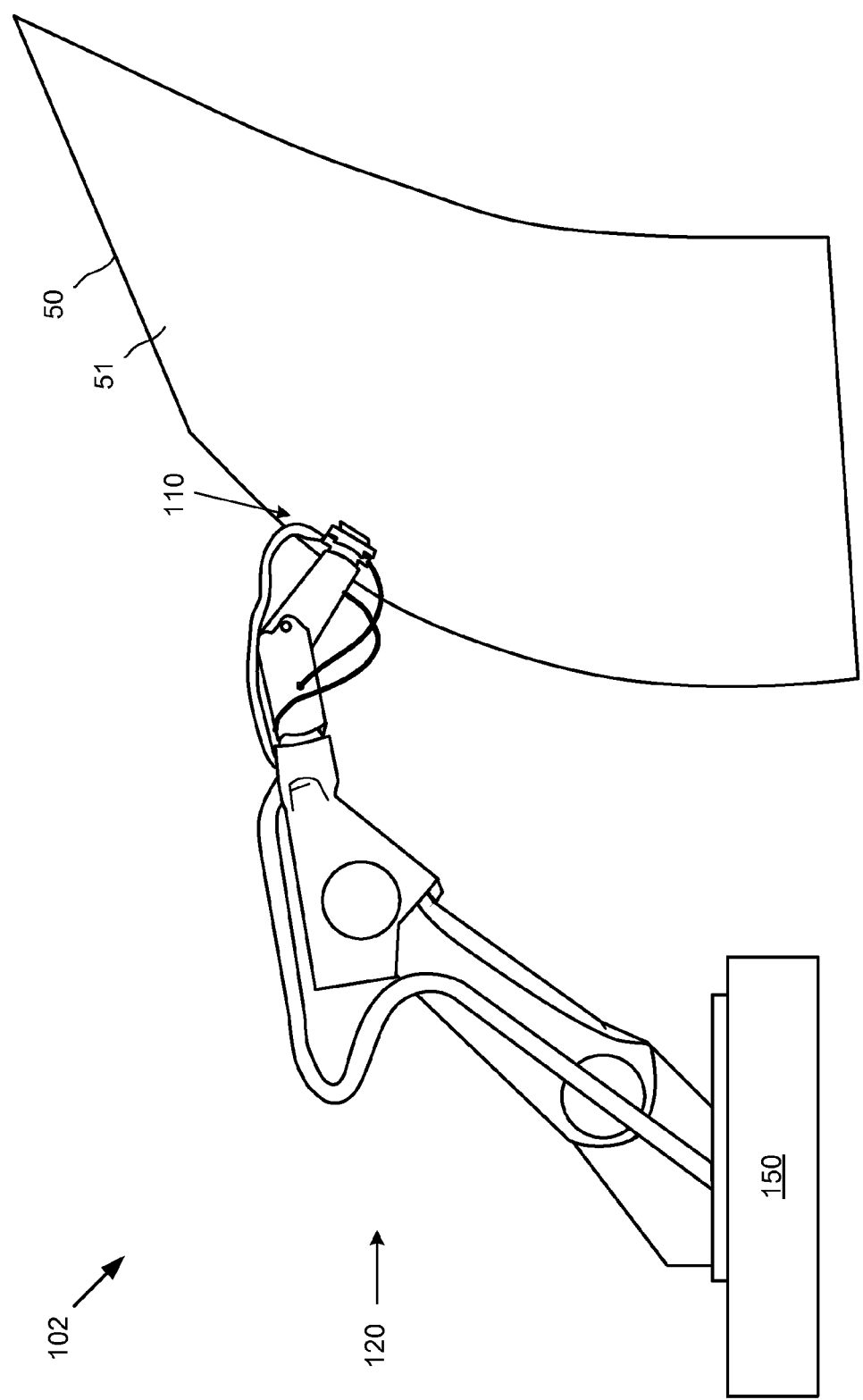

NON-DESTRUCTIVE ULTRASONIC INSPECTION APPARATUS, SYSTEMS, AND METHODS

FIELD

This disclosure relates generally to detecting structural characteristics of a component, and more particularly to detecting abnormalities or damage in a component using an ultrasonic inspection probe.

BACKGROUND

Structures experiencing loads or exposed to various environmental factors are susceptible to damage, such as cracking, corrosion, delamination, and the like. Additionally, some structures include abnormalities formed during a manufacturing process. Damage to and abnormalities in structures may lead to aesthetic flaws, structural degradation, inefficiencies, poor performance, and even catastrophic failure. Accordingly, the detection of damage to structures may be desirable to mitigate or prevent the occurrence of such negative consequences. In some circumstances, the negative consequences of damage to the structure can be mitigated or prevented through detection and repair of the damage.

Some structures include features that are particularly susceptible to damage. For example, cracks tend to form at and emanate from fastener holes in surfaces of certain structures, such as aircraft.

SUMMARY

The subject matter of the present application has been developed in response to the present state of the art, and in particular, in response to the problems associated with, and the need to, detect damage, such as crack formations, and abnormalities, such as delamination or voids, in various structures, including aircraft, that have not yet been fully solved by currently available techniques. Accordingly, the subject matter of the present application has been developed to provide an apparatus, system, and method for detecting abnormalities and damage in a structure that overcome at least some of the above-discussed shortcomings of prior art techniques.

According to one embodiment, a system for inspecting a component includes an ultrasonic inspection probe that has a component surface interface. The system also includes a robotic device with an end effector coupled to the ultrasonic inspection probe. The robotic device is automatably controllable to move the ultrasonic inspection probe across a surface of the component. Additionally, the system includes an angle sensor subsystem coupled between the ultrasonic inspection probe and the end effector. The angle sensor subsystem is configured to operably detect an actual orientation of the end effector relative to a presently inspected portion of the surface of the component. The system includes a controller configured to receive orientation data from the angle sensor subsystem, the orientation data comprising the actual orientation of the end effector, compare the actual orientation to a desired orientation, and control the robotic device to adjust an orientation of the end effector to be in the desired orientation.

In one implementation of the system, the desired orientation is associated with a longitudinal axis of the end effector being perpendicular to the presently inspected portion of the surface of the component.

According to one implementation, the system further includes an articulation subsystem coupled between the inspection probe and the end effector. The articulation subsystem is configured to operably maintain the component surface interface properly engaged with the presently inspected portion of the surface of the component. The articulation subsystem includes a two-axis gimbal structure coupled between the ultrasonic inspection probe and the end effector in an implementation. The two-axis gimbal structure can be configured to passively absorb pitch and roll movement of the ultrasonic inspection probe. In an implementation, the articulation subsystem further includes a pneumatic actuator coupled between the two-axis gimbal structure and the end effector. The pneumatic actuator is configured to passively absorb movement of the ultrasonic inspection probe, via the two-axis gimbal structure, along an axis substantially perpendicular to the presently inspected portion of the surface of the component. The angle sensor subsystem includes a plurality of transducers coupled to the two-axis gimbal structure in an implementation. According to one implementation, the plurality of transducers includes a rotary variable differential transformer (RVDT) coupled to each axis of the two-axis gimbal structure.

According to yet one implementation, the ultrasonic inspection probe includes a housing, an ultrasonic array coupled to the housing, and a component surface interface of the housing. The component surface interface includes a liquid couplant port, an engagement lip engageable with a surface of the component, and at least one vacuum port. The engagement lip circumferentially circumscribes the liquid couplant port and the at least one vacuum port circumferentially circumscribes the engagement lip. The at least one vacuum port is fluidly coupleable with a vacuum source. The ultrasonic inspection probe also includes a liquid couplant chamber disposed between the ultrasonic array and the liquid couplant port of the component surface interface. The liquid couplant chamber is in fluid communication with the liquid couplant port and the liquid couplant chamber is fluidly coupleable with a liquid couplant supply. Additionally, the ultrasonic inspection probe includes an articulation subsystem coupled to the housing and configured to operably maintain the engagement lip of the component surface interface properly engaged with the presently inspected portion of the surface of the component.

In yet one embodiment, an apparatus for inspecting a component includes a housing, an ultrasonic array coupled to the housing, and a component surface interface of the housing. The component surface interface includes a liquid couplant port, an engagement lip engageable with a surface of the component, and at least one vacuum port. The engagement lip circumferentially circumscribes the liquid couplant port and the at least one vacuum port circumferentially circumscribes the engagement lip. The at least one vacuum port is fluidly coupleable with a vacuum source. The apparatus also includes a liquid couplant chamber disposed between the ultrasonic array and the liquid couplant port of the component surface interface. The liquid couplant chamber is in fluid communication with the liquid couplant port and the liquid couplant chamber is fluidly coupleable with a liquid couplant supply. The apparatus further includes an articulation subsystem coupled to the housing and configured to operably maintain the component surface interface properly engaged with a presently inspected portion of the surface of the component.

In one implementation, the apparatus defines a central axis extending from the ultrasonic array and through the liquid couplant chamber and liquid couplant port. The articulation subsystem is configured to operably maintain the central axis substantially perpendicular to the presently inspected portion of the surface of the component. According to an implementation, the liquid couplant chamber includes a substantially uniform cross-sectional shape along the central axis and through the liquid couplant port.

According to one implementation, the engagement lip of the component surface interface is protruded relative to the at least one vacuum port so as to be positionable closer to the surface of the component relative to the at least one vacuum port.

In an implementation, the housing is coupled to an end effector of a robotic device. The robotic device is automatably controllable to move the apparatus across the surface of the component. The articulation subsystem includes a two-axis gimbal structure coupled between the housing and the end effector in one implementation. The two-axis gimbal structure is configured to passively absorb pitch and roll movement of the housing. The articulation subsystem further includes a pneumatic actuator coupled between the two-axis gimbal structure and the end effector. The pneumatic actuator is configured to passively absorb movement of the housing, via the two-axis gimbal structure, along an axis substantially perpendicular to the presently inspected portion of the surface of the component.

According to an implementation, the apparatus also includes an angle sensor subsystem coupled to the two-axis gimbal structure. The angle sensor subsystem is configured to detect an actual orientation of the end effector relative to the presently inspected portion of the surface of the component. The apparatus further includes a controller configured to receive orientation data from the angle sensor subsystem corresponding to the actual orientation of the end effector, compare the actual orientation to a desired orientation, and control the robotic device to adjust the actual orientation of the end effector to be in the desired orientation. The desired orientation includes a longitudinal axis of the end effector perpendicular to the presently inspected portion of the surface of the component. The angle sensor subsystem may be a plurality of transducers coupled to the two-axis gimbal structure. The plurality of transducers includes an RVDT coupled to each axis of the two-axis gimbal structure in one implementation.

According to another embodiment, a method for inspecting a component includes robotically moving an ultrasonic inspection probe across a surface of the component to inspect structural characteristics of the component. Moving the ultrasonic inspection probe may include automatably controlling a robotic device with an end effector to which the ultrasonic inspection probe is coupled. The method includes detecting an actual orientation of the end effector relative to a presently inspected portion of the surface of the component. Detecting the actual orientation of the end effector includes receiving orientation data from an angle sensor subsystem that is coupled between the ultrasonic inspection probe and the end effector. Additionally, the method includes comparing the actual orientation to a desired orientation, and controlling the robotic device to adjust the actual orientation of the end effector to be in the desired orientation.

In yet one embodiment, a controller for inspecting a component includes a movement module configured to implement a movement pattern of an ultrasonic inspection probe across a surface of the component by controlling a robotic device with an end effector to which the ultrasonic inspection probe is coupled. The controller includes a data module configured to receive structural characteristic data detected by the ultrasonic inspection probe. Additionally, the controller includes an orientation module configured to detect an actual orientation of the end effector of the robotic device relative to a presently inspected portion of the surface of the component, compare the actual orientation to a desired orientation, and control the robotic device to adjust the actual orientation of the end effector to be in the desired orientation.

According to an implementation, the controller further includes a learning module configured to incorporate predetermined orientation adjustments of the movement pattern at predetermined locations across the surface of the component from a previously performed inspection procedure into the movement pattern.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which:

FIG. 2 is a perspective view of a system for inspecting a component, according to one embodiment;

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1A:
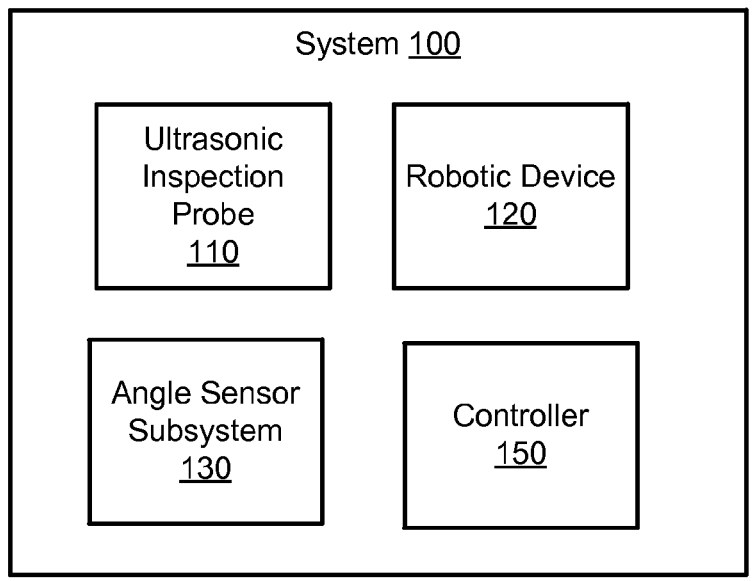
FIG. 1A is a schematic block diagram of a system for inspecting a component, the system including an ultrasonic inspection probe, a robotic device, an angle sensor subsystem, and a controller, according to one embodiment.

FIG. 1A is a schematic block diagram of a system 100 for inspecting a component. The component 50 to be inspected may be or form part of any of various structures, such as a vehicle, a building, a bridge, and aircraft, etc. According to one embodiment, the system 100 includes an ultrasonic inspection probe 110, a robotic device 120, an angle sensor subsystem 130, and a controller 150. Generally, the ultrasonic inspection probe 110 is coupled to the robotic device 120 and the robotic device 120 is controlled by the controller 150 to position the ultrasonic inspection probe 110 in a desired inspection position relative to a surface of the component being inspected. The angle sensor subsystem 130 is configured to monitor the angular position of the inspection probe 110 in order to maintain the inspection probe 110 in the desired position. Once the ultrasonic inspection probe 110 is in the desired inspection position, the controller 150 actuates the robotic device 120 in order to move the ultrasonic inspection probe 110 along and across surface of the component (as described in greater detail with respect to FIG. 2).

Figure 1B:
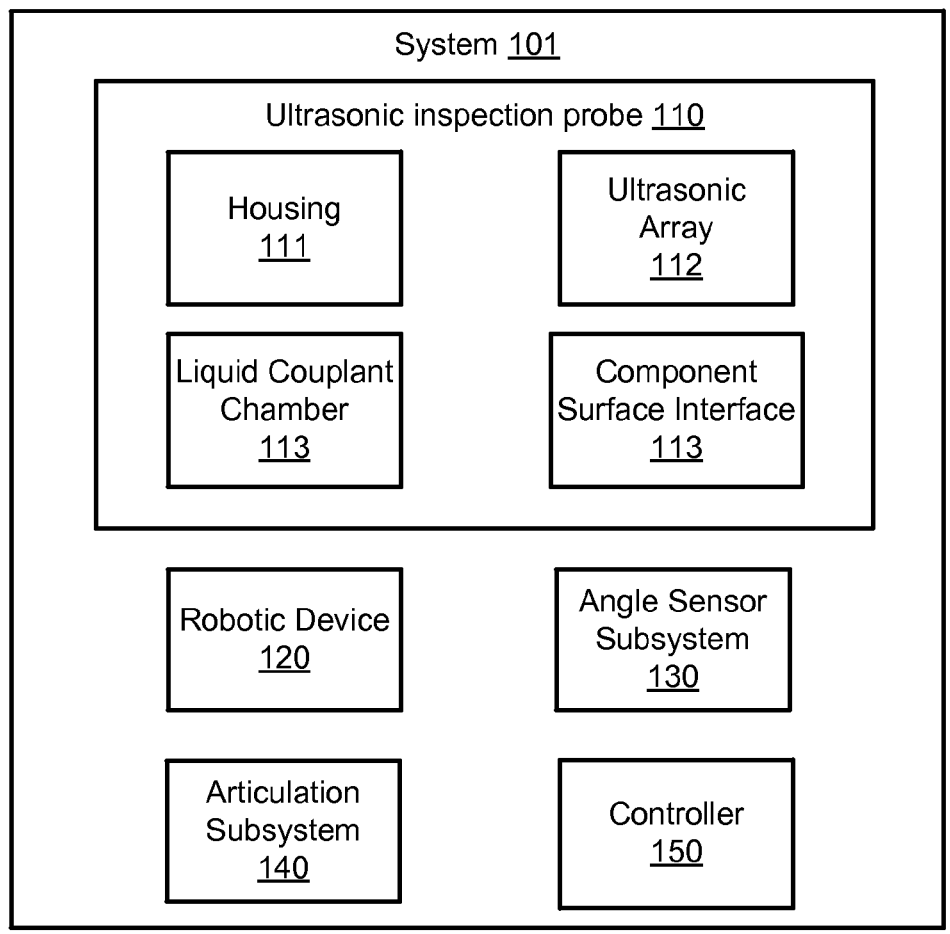
FIG. 1B is a schematic block diagram of a system for inspecting a component the system including ultrasonic inspection probe, a robotic device, an articulation subsystem, an angle sensor subsystem, and a controller, according to one embodiment.

FIG. 1B is a schematic block diagram of another embodiment of a system 101 for inspecting a component, the system 101 including the ultrasonic inspection probe 110, the robotic device 120, the angle sensor subsystem 130, an articulation subsystem 140, and the controller 150. The inspection probe 110, the robotic device 120, the angle sensor subsystem 130, and the controller 150 may be substantially the same as described above with reference to FIG. 1A. The articulation subsystem 140, according to one embodiment, is configured to further facilitate the maintenance of the proper position of the ultrasonic inspection probe 110. The articulation subsystem 140, as described in greater detail below with reference to FIGS. 4 and 5, dampens and/or absorbs certain features or irregularities in the surface of the component being inspected in order to allow the ultrasonic inspection probe 110 to remain properly engaged on the surface of the component.

FIG. 2 is a perspective view of one embodiment of the system 102 for inspecting the component 50. Referring to FIG. 2, the system 102 includes the ultrasonic inspection probe 110, which is coupled to the robotic device 120. The robotic device 120 can be controlled by the controller 150. More specifically, the robotic device 120 is controlled by the controller 150 to position the ultrasonic inspection probe 110 in a desired inspection position relative to a surface 51 of the component 50 in order to non-destructively inspect the structure. As described below and according to one embodiment, the desired inspection position can be a position in which an ultrasonic transducer array of the ultrasonic inspection probe 110 is perpendicular to the outer surface 51 of the component. With the ultrasonic inspection probe 110 in the desired inspection position, the robotic device 120, actuated by the controller 150, operably moves the ultrasonic inspection probe 110 along and across the surface 51 of the component 50.

As described in greater detail below with reference to FIGS. 6A and 6B, the ultrasonic array housed within ultrasonic inspection probe 110 transmits an ultrasonic signal directed at the component 50. In one embodiment, the ultrasonic inspection probe 110 further includes means for utilizing a liquid couplant, such as water, oil, propylene glycol, glycerin, gel, and the like, to facilitate and promote the transmission and propagation of the ultrasonic signal/waves.

The controller 150, as depicted in FIG. 2, is coupled to the robotic device 120. In another embodiment, the controller 150 may be integrated or coupled to a computer or a computer network that is electronically coupled to the robotic device 120. In a further embodiment, the controller 150 may have various modules that are implemented using various electronic devices. Additional details relating to the controller 150 are included below with reference to FIGS. 7A and 7B. As depicted in FIG. 2, the robotic device 120 may be a robotic arm that is rotatable, pivotable, and/or extendable in a variety of different manners in order to position the ultrasonic inspection probe 110 in a plurality of positions. For example, in one embodiment the robotic device 120 is a robotic arm manufactured by Kuka®.

The component 50 can be any of various components made from any of various materials. In some implementations, the component 50 is made from a metal, such as steel and aluminum. In other implementations, the component 50 is made from a non-metal, such as graphite, composite, ceramic, polymer, and the like. In one embodiment, the component has a 3-dimensional structure that can be any of various 3-dimensional structures. For example, the component 50 may be non-flat or substantially curved and/or may include one or more protrusions that protrude relative to a flat or substantially non-flat plane of reference. Additionally, the component 50 may be double-sided and the system 102 may be configured to inspect both sides of the component 50.

Figure 3A:
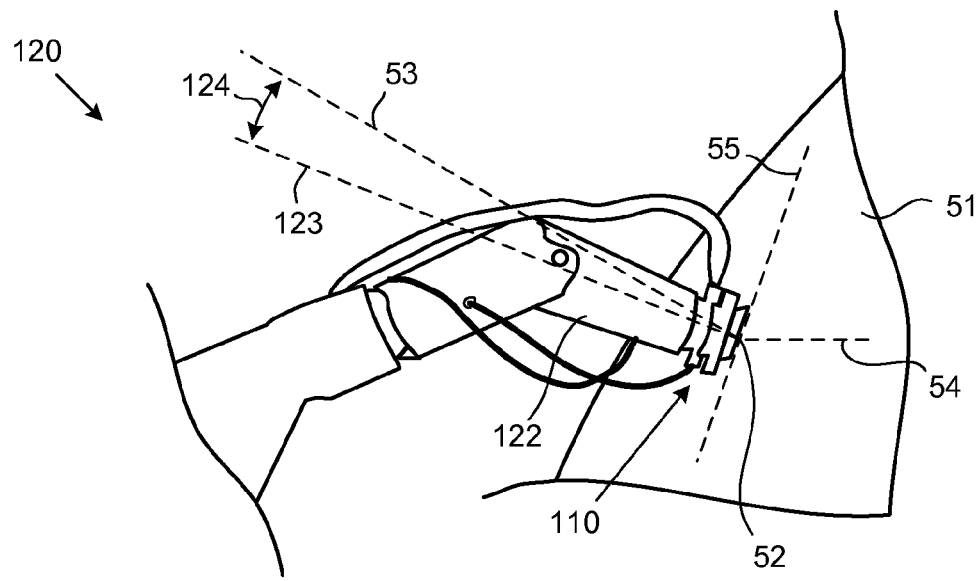
FIG. 3A is a partial perspective view of an end effector of a robotic device having an actual orientation that is different from a desired orientation, according to one embodiment.
Figure 3B:
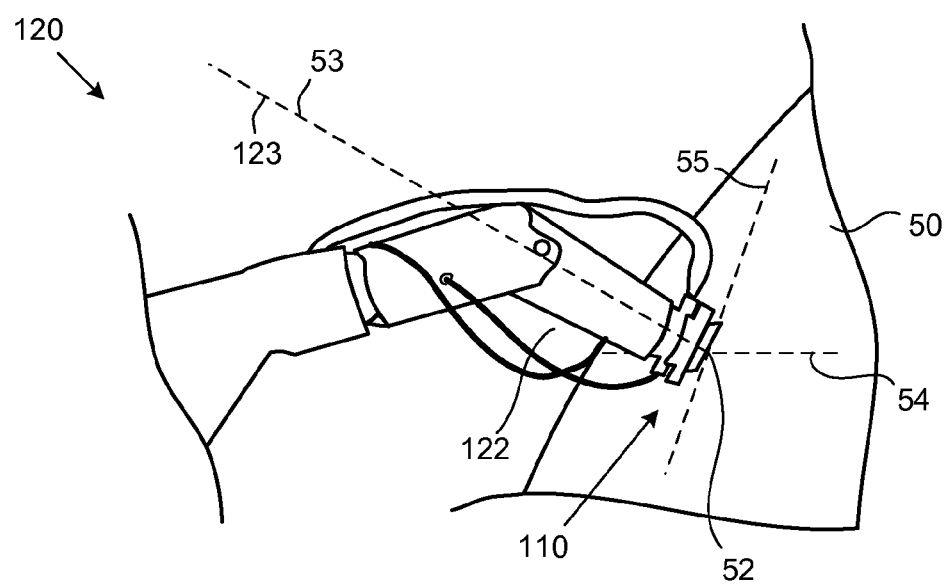
FIG. 3B is a partial perspective view of an end effector of a robotic device having an actual orientation that is the same as a desired orientation, according to one embodiment.

FIG. 3A is a partial perspective view of one embodiment of an end effector 122 of the robotic device 120, with the end effector being having an actual orientation that is different from a desired orientation. FIG. 3B is a partial perspective view of the end effector 122 of the robotic device 120 having an actual orientation that is the same as the desired orientation. The ultrasonic inspection probe 110 is coupled to the end effector 122 of the robotic device 120. Upon operation, the ultrasonic inspection probe 110 moves across the surface 51 of the component 50. During operation, the region or portion of the surface 51 of the component 50 that is instantaneously inspected is referred to herein as the presently inspected portion 52 of the component 50. FIGS. 3A and 3B show three coordinate axis 53, 54, 55 relative to the presently inspected portion 52. Two of the axis, the x-axis 54 and the y-axis 55, extend in their respective directions substantially tangentially from the presently inspected portion 52 of the component 50. The normal axis 53 extends perpendicularly away from the x-axis 54 and y-axis 55.

In one embodiment, the end effector 122 and the coupled ultrasonic inspection probe 110 desirably remain in a substantially perpendicular orientation, with respect to the presently inspected portion 52 of the component 50, as the ultrasonic inspection probe 110 moves across and along the surface 51 of the component 50. In other words, the system includes the angle sensor subsystem 130 in order to maintain a longitudinal axis 123 of the end effector 122 of the robotic device 120 in a desired orientation relative to the presently inspected portion 52 of the component 50. For example, in one embodiment the desired orientation is substantially parallel to the normal axis 53 (i.e., perpendicular to the tangential coordinate axis 54, 55). FIG. 3A shows an angle 124 between the longitudinal axis 123 of the end effector 122 of the robotic device 120 and the normal axis 53. In such an embodiment, the actual position of the end effector 122 of the robotic device 120 is different from the desired orientation. Accordingly, the system includes, according to one embodiment, the angle sensor subsystem 130. As described below, the angle sensor subsystem 130 is configured to detect the offset orientation of the end effector 122 and report such an offset to the controller 150. The controller 150 is then able to send actuation commands to the robotic device 120 to reposition and/or reorient the robotic device 120, specifically the end effector 122 of the robotic device 120, so that the longitudinal axis 123 is substantially parallel to the normal axis 53, as depicted in FIG. 3B.

As described above, the robotic device may be pivotable, rotatable, and extendable. Accordingly, depending on the detected actual orientation of the end effector 122 relative to the presently inspected portion 52 of the surface 51 of the component and the offset between the actual orientation and the desired orientation, the controller 150 may send various actuation commands to the robotic device 120 in order to correct the actual orientation of the end effector 122 (i.e., actuate the robotic device 120 so that the actual orientation matches the desired orientation). The type of adjustments to the orientation of the end effector 122 may include lateral adjustments, pitch adjustments, roll adjustments, extension adjustments, and height adjustments, among others.

The angle sensor subsystem 130 may include various sensors and/or transducers that detect the actual orientation of the end effector 122 with respect to the presently inspected portion 52 of the component and report any difference between the actual orientation and the desired orientation of the end effector 122. For example, in one embodiment the angle sensor subsystem 130 includes a rotary variable differential transformer (RVDTs). An RVDT is a type of electrical transformer that detects and/or measures angular displacement. Accordingly, in one embodiment, the system 100 may include one or more RVDTs coupled at the point(s) where the end effector 122 is coupled to the ultrasonic inspection probe 110. In another embodiment, the angle sensory subsystem 130 may include other sensors that are capable of detecting the angled orientation of an object with respect to another object (i.e., a surface of the object). For example, an optical sensor mechanism may be implemented to detect the actual orientation of the end effector 122 with respect to the presently inspected portion 52 of the component 50.

Figure 4:
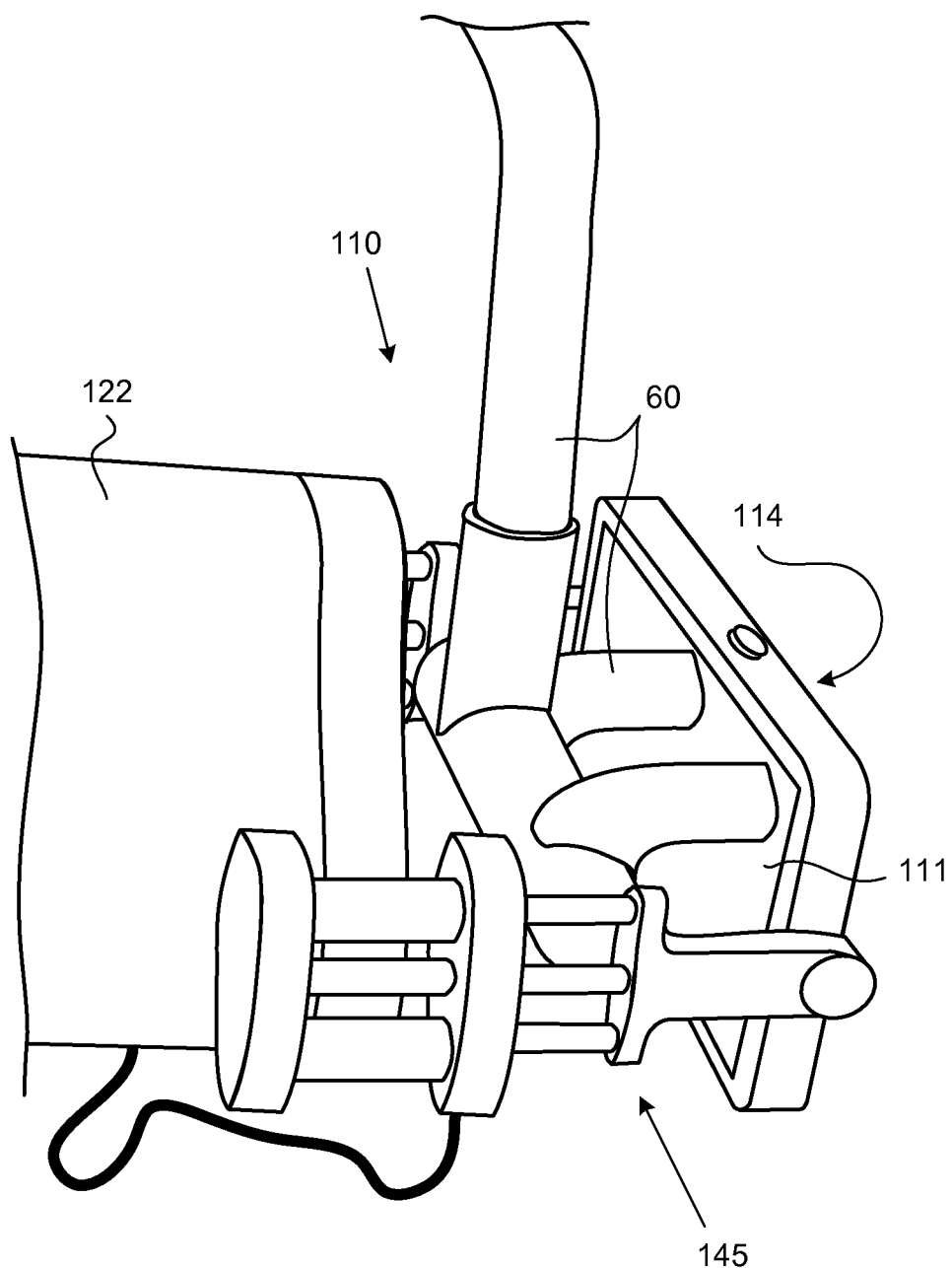
FIG. 4 is a perspective view of an ultrasonic inspection probe coupled to an end effector of a robotic device and a pneumatic actuator of an articulation subsystem, according to one embodiment.

FIG. 4 is a perspective view of one embodiment of the ultrasonic inspection probe 110 coupled to the end effector 122 of the robotic device 120 and a pneumatic actuator 145 of an articulation subsystem 140. In one embodiment, the ultrasonic inspection probe 110 may employ a liquid couplant between the ultrasonic array housed within the housing 111 and the surface of the component being inspected. Accordingly, various tubes, pipes, and/or manifold assemblies 60 handling the liquid couplant may be included with or coupleable with the ultrasonic inspection probe 110. Additionally, included with or coupleable with the ultrasonic inspection probe 110 may be vacuum lines and/or a vacuum source for vacuuming excess liquid couplant. The liquid couplant transmission lines and/or the vacuum lines may include one or more liquid couplant ports and one or more vacuum ports disposed on a component surface interface 114 of the ultrasonic inspection probe 110. Details relating to one specific embodiment of an ultrasonic inspection probe that utilizes a liquid couplant in a vacuum system are included below with reference to FIGS. 5-6B.

In one embodiment, the system for inspecting the component may also include an articulation subsystem. The articulation subsystem may be configured to dampen and/or absorb the effect that certain features or irregularities in the surface of the component 50 have on inspection process. For example, when a column of liquid couplant is employed between the ultrasonic inspection probe 110 and the surface 51 of the component 50 to promote the propagation and transmission of an ultrasonic signal, it may be beneficial for the component surface interface 114 to remain substantially parallel to the presently inspected portion 52 of the surface 51 of the component 50 in order to maintain a consistent column of liquid couplant (i.e., prevent excessive liquid couplant leakage).

In one embodiment, the articulation subsystem may include a passive actuator that absorbs unwanted and/or unexpected movement along the longitudinal axis 123 of the end effector 122. For example, as depicted in FIG. 4, a pneumatic actuator 145 may be coupled between the end effector 122 in the ultrasonic inspection probe 110. In such an embodiment, the pneumatic actuator 145 helps to maintain the component surface interface 114 of the ultrasonic inspection probe 110 appropriately engaged on the surface 51 of the component 50. The articulation subsystem may further include assemblies and/or mechanisms that dampen pitch and roll type movement of the ultrasonic inspection probe 110 (e.g., a gimbal structure).

Figure 5:
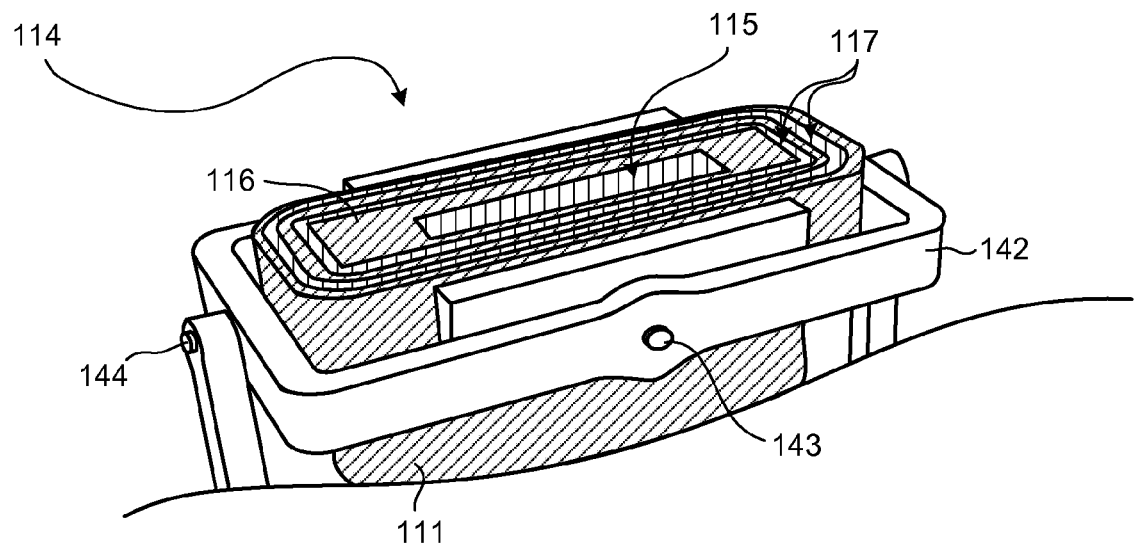
FIG. 5 is a perspective view of a component surface interface of an ultrasonic inspection probe and a two-axis gimbal structure of an articulation subsystem, according to one embodiment.

FIG. 5 is a perspective view of one embodiment of a component surface interface 114 of the ultrasonic inspection probe 110 and an articulation subsystem that includes a two-axis gimbal structure 142. The gimbal structure 142, according to one embodiment, includes a first axis 143 and a second axis 144 that dampen and/or absorb pitch and roll type movement of the component surface interface 114 of the ultrasonic inspection probe 110. As defined herein, the component surface interface 114 of the ultrasonic inspection probe 110 is this section/surface of the ultrasonic inspection probe that engages or at least faces the presently inspected portion 52 of the surface 51 of the component 50.

In the depicted embodiment, the component surface interface 114 includes a couplant port 115 and at least one vacuum port 117. In one embodiment, the component surface interface 114 further includes an engagement lip 116 that circumferentially circumscribes the liquid couplant port 115. The engagement lip 116 is defined herein as the surface that engages the presently inspected portion 52 of the surface 51 of the component and prevents excessive liquid couplant leakage from a liquid couplant chamber (not shown in FIG. 5) of the housing 111 of the ultrasonic inspection probe 110. In one embodiment the housing 111, or at least a portion of the housing 111 such as the engagement lip 116, is made from a compliant material that flexes when engaged upon the surface 51 of the component 50. In such an embodiment, the flexing nature of the engagement lip 116 promotes the proper engagement between the surface 51 of the component 50 and the ultrasonic inspection probe 110, thereby preventing excessive liquid couplant leakage and improving the accuracy of the ultrasonic inspection technique. Accordingly, according to one embodiment, the engagement lip 116 circumferentially circumscribes the liquid couplant port 115 and the at least one vacuum port 117 circumferentially circumscribes the engagement lip 116. In such an embodiment, any liquid couplant that leaks between the engagement lip 116 and the surface 51 of the component 50 is suctioned through the at least one vacuum port 117 to prevent liquid couplant from running down/across the surface 51 of the component 50 and to maintain the surface 51 of the component 50 substantially dry and free from excessive liquid couplant. In one embodiment, when the surface 51 of the component 50 is substantially dry and free from excessive liquid couplant, subsequent inspection procedures and/or subsequent manufacturing/assembly procedures may be more easily implemented with the component 50 because there is no need to air dry and/or clean the surface 51 of the component 50.

As briefly described above, RVDTs, or other such devices, may be coupled to the first axis 143 and/or second axis 144 of the gimbal structure to detect the angled orientation of the end effector 122 of the robotic device 120 with respect to the presently inspected portion 52 of the surface 51 of the component 50. For example, the component surface interface 114 of the ultrasonic inspection probe 110 may still be maintained substantially parallel to the presently inspected portion 52 of the surface 51 of the component 50 via the gimbal structure 142 even when the longitudinal axis 123 of the end effector 122 of the robotic device 120 is not perpendicular to the presently inspected portion 52 of the surface 51 of the component 50. However, the angle sensor subsystem 130 may detect the non-perpendicular longitudinal axis 123 of the end effector 122 and may send such a notification to the controller 150. The controller 150 may then send actuation commands to the robotic device 120 to adjust the position and orientation of the end effector 122.

Figure 6A:
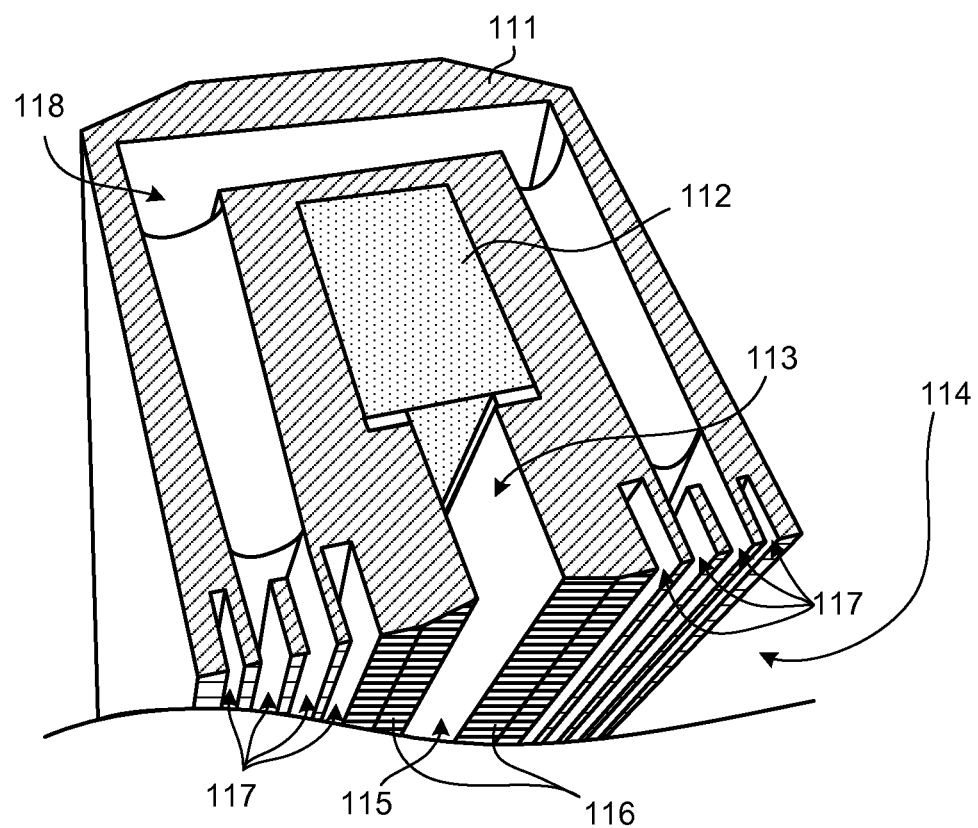
FIG. 6A is a partial, cross-sectional perspective view of an ultrasonic inspection probe having a liquid couplant chamber, according to one embodiment.
Figure 6B:
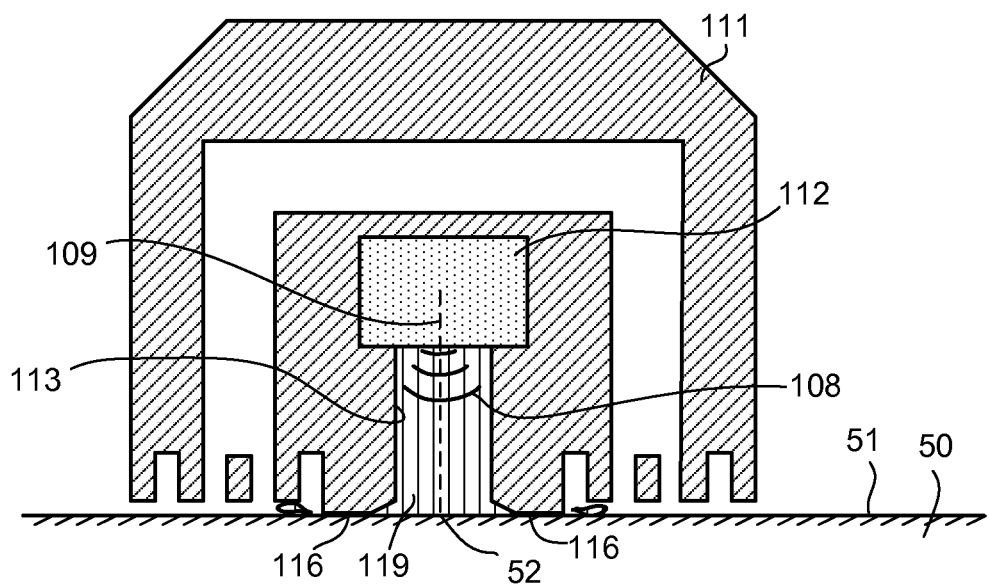
FIG. 6B is a cross-sectional view of an ultrasonic inspection probe having an engagement lip proximate a surface of a component, according to one embodiment.

FIG. 6A is a partial, cross-sectional perspective view of one embodiment of the ultrasonic inspection probe 110 having a liquid couplant chamber 113 and FIG. 6B is a cross-sectional view of the ultrasonic inspection probe having the engagement lip 116 proximate the presently inspected portion 52 of the surface 51 of the component 50. In the depicted embodiment, the ultrasonic inspection probe 110 includes a housing 111 within which an ultrasonic array 112 is housed. The housing 111 of the ultrasonic inspection probe 110 further includes a liquid couplant chamber 113 disposed between the ultrasonic array 112 and the component surface interface 114. Although not depicted, the housing 111 may include liquid couplant supply lines, coupleable with a liquid couplant supply source, that operably deliver liquid couplant to the liquid couplant chamber 113. In one embodiment, the liquid couplant chamber 113 is maintained at a positive pressure in order to promote a uniform/consistent propagation medium for the ultrasonic signal. As described above, during operation of the ultrasonic inspection probe 110, a substantially uniform column of liquid couplant 119 may be maintained within the liquid couplant chamber 113, thereby facilitating the transmission and propagation of an ultrasonic signal 108 between the ultrasonic array 112 and the presently inspected portion 52 of the surface 51 of the component 50.

The ultrasonic array 112 may include multiple wave transducers that can be any of various wave transducers for emitting and receiving ultrasonic signals 108. According to some embodiments, the wave transducers of the ultrasonic array 112 emit and receive ultrasonic waves. Generally, the ultrasonic signal 108 generated and emitted by the ultrasonic array are transmitted into the component 50. After passing through the column of liquid couplant 119, the ultrasonic signal 108 propagates through the component 50 from the outer surface 51 (e.g., front surface) to an opposing back surface. Portions of the signal 108 may reflect off the outer surface 51, the inner structure, and the back surface of the component 50. The reflected waves pass through the column of liquid couplant and are received by the wave transducers of the ultrasonic array 112. The pulse characteristics (e.g., amplitude) of the ultrasonic signal 108 generated by the wave ultrasonic array 112 are compared to the pulse characteristics of the reflected waves received by the ultrasonic array (e.g. after passing through the component 50) to determine if defects exist in the structure. The type of wave transducers utilized for a specific embodiment of the ultrasonic array may be selected according to the type of structure that is being inspected. For example, certain wave transducers may be comparatively better-suited for metallic structures while other wave transducers may be comparatively better-suited for composite structures.

The engagement lip 116, according to one embodiment, may be slightly protruded so as to be comparatively closer to the surface 51 of the component 50 then the vacuum ports 117. As described above, the vacuum ports 117 are fluidly coupled to the interior vacuum cavity 118 within the housing 111 of the ultrasonic inspection probe 110. The number, size, configuration, shape, and dimensions of the vacuum ports 117 may be selected according to the specifics of a given application.

According to one embodiment, the maintenance of the proper orientation of the ultrasonic inspection probe 110 with respect to the present inspected portion 52 of the surface 51 of the component 50 is important to an accurate inspection. Accordingly, the angle sensor subsystem 130 and the articulation subsystem 140 may both be implemented to facilitate maintaining the proper orientation of the ultrasonic inspection probe 110. Not only with the proper orientation of the ultrasonic inspection probe 110 prevent leakage of liquid couplant 119, the detection of structural characteristic data relating to the reflected waves from a properly oriented ultrasonic inspection probe will be comparatively more accurate. In other words, an ultrasonic inspection probe that is offset from a desire orientation may potentially result in any accurate and/or skewed structural characteristic data of the component 50.

A central axis 109 extends from the ultrasonic array 112 through the liquid couplant chamber 113 and the liquid couplant port 115. In one embodiment, the proper position of the ultrasonic inspection probe 110 is when the central axis 109 is substantially perpendicular to the presently inspected portion 52 of the surface 51 of the component 50. Put differently, in the proper position the central axis 109 is parallel to the normal axis 53 shown in FIGS. 3A and 3B.

Generally, the articulation subsystem 140 maintains proper engagement between the component surface interface 114 of the ultrasonic inspection probe 110 despite inconsistencies/irregularities in the surface 51 of the component 50 and the angle sensor subsystem 130 actively detects offsets between an actual orientation of the end effector 122 of the robotic device 120 and, via the controller 150, actively actuates the robotic device 120 to adjust the actual orientation of the end effector 122 to be in the desired orientation. With one or both of the subsystems, the ultrasonic inspection probe 110 of the present disclosure is able to, when compared with most conventional inspection devices, move across the surface 51 of the component 50 at a comparatively higher speed while still maintaining the proper position/orientation of the ultrasonic inspection probe 110.

Figure 7A:
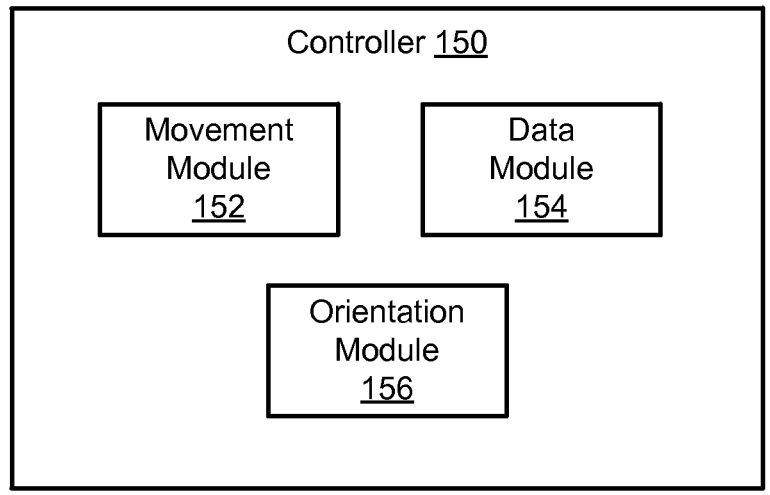
FIG. 7A is a schematic block diagram of a controller for controlling an inspection of a component, according to one embodiment.

FIG. 7A is a schematic block diagram of one embodiment of the controller 150 for controlling an inspection of the component 50. The controller 150, according to one embodiment, includes a movement module 152, a data module 154, and an orientation module 156. The movement module 152 is configured to implement a movement pattern of the ultrasonic inspection probe 110 across a surface 51 of the component 50 by controlling the robotic device 120, with the ultrasonic inspection probe 110 coupled to the end effector 122. The movement module 152 may include pre-programmed/predetermined movement patterns and associated robotic algorithms for actuating the movement pattern with robotic device.

The data module 154 is configured to receive structural characteristic data detected by the ultrasonic inspection probe 110. In other words, the data module 154 receives output signals from the ultrasonic array 112. According to some embodiments, the data module 154, or separate analysis module (not shown), utilizes the structural characteristic data to detect the presence of damage in the structure of the component 50. The data module 154 can use any of various methods and/or apply any of various algorithms for detecting damage based on the sensed structural characteristic data. In certain embodiments, the data module 154 detects damage to the structure by applying the sensed structural characteristic data to a baseline-less model without relying on predetermined or known baselines.

However, in yet some embodiments, the data module 154 detects damage by applying the structural characteristic data to a baseline model by relying on predetermined or known baseline waveforms. For example, in one embodiment, the data module 154 compares the structural characteristic data with expected data or baseline to detect the presence of damage in the structure of the component 50. Accordingly, variations in the structural characteristic data compared to the expected data indicates abnormalities or damage (e.g., cracking) in the structure of the component 50.

The orientation module 156 is configured to detect the actual orientation of the end effector 122 relative to the presently inspected portion 52 of the surface 51 of the component 50 based on the sensed structural characteristic data. Once the actual orientation of the end effector 122 is determined, the orientation module 156 compares the actual orientation to the desired orientation sends actuation commands to the robotic device 120 to adjust the actual orientation of the end effector 122 so as to be in the desired orientation.

Figure 7B:
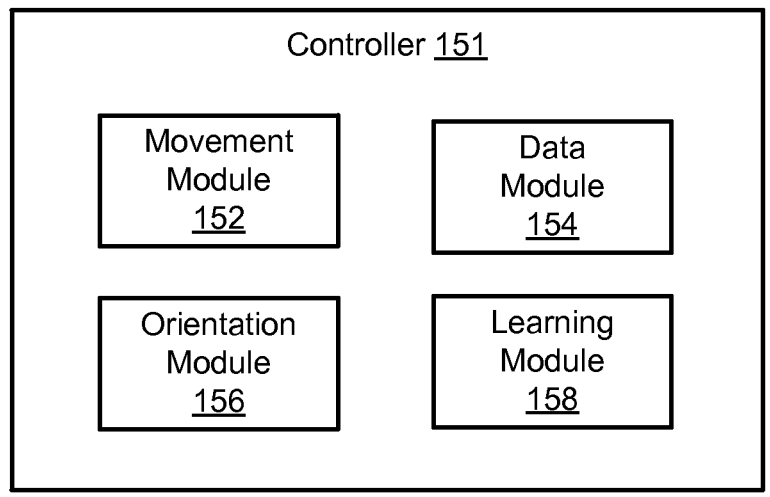
FIG. 7B is a schematic block diagram of a controller for controlling an inspection of a component, according to another embodiment.

As depicted in FIG. 7B, in one embodiment the controller 151 may include the previously described modules 152, 154, 156 in addition to a learning module 158. The learning module 158 may be configured to incorporate predetermined orientation adjustments to the end effector 122 relative to predetermined locations across the surface of the component from a previously performed inspection procedure on the component into the movement pattern of the movement module. In other words, the learning module 158 may interact with the movement module 152 to change/alter the movement pattern in the movement algorithms that is sent to the robotic device 120 in order to improve the positioning accuracy of the end effector 122 of the robotic device 120.

Figure 8:
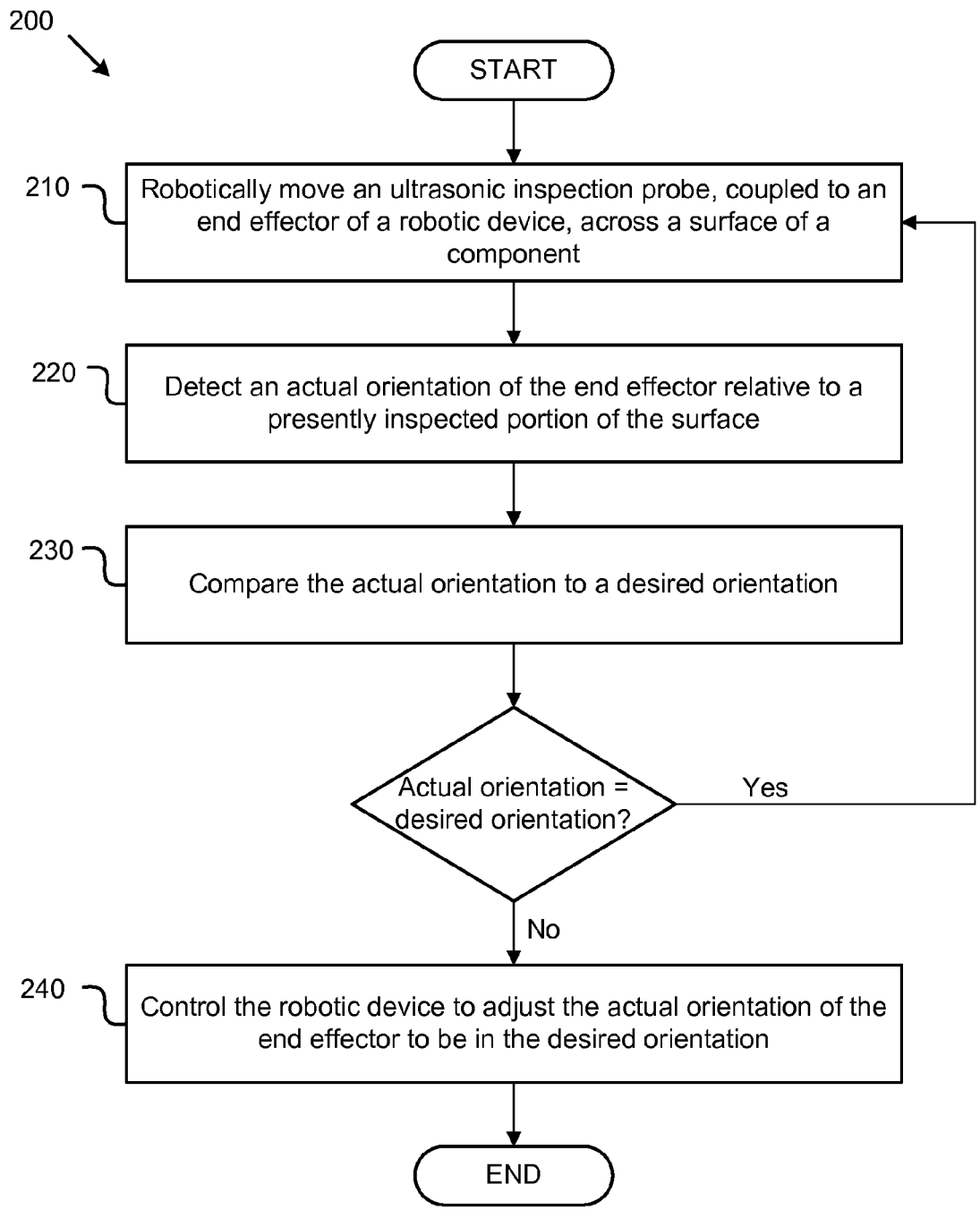
FIG. 8 is a schematic flow chart diagram of a method for inspecting a component, according to one embodiment.

FIG. 8 is a schematic flow chart diagram of one embodiment of a method 200 for inspecting the component. According to one embodiment, the method 200 for detecting damage in a structure can be executed by the systems and apparatus described herein, or other systems and apparatus. The method 200 includes robotically moving an ultrasonic inspection probe across a surface of the component to inspect structural characteristics of the component at 210. In one embodiment, moving the ultrasonic inspection probe includes automatably controlling a robotic device having an end effector to which the ultrasonic inspection probe is coupled.

The method 200 further includes detecting an actual orientation of the end effector relative to a presently inspected portion of the surface of the component at 220. According to one embodiment, detecting the actual orientation of the end effector includes receiving orientation data from an angle sensor subsystem that is coupled between the ultrasonic inspection probe and the end effector. The method 200 further includes comparing the actual orientation of the end effector to a desired orientation at 230 and controlling the robotic device to adjust the actual orientation of the end effector to be in the desired orientation at 240.

In one embodiment, the method 200 may further include adjusting the actual orientation of the end effector according to predetermined orientation adjustments at predetermined locations across the surface of the component from a previously performed inspection of the component. For example, the controller may have detected, from a previously performed inspection of a component (e.g., an aircraft), locations/points across the surface of the component that required active adjustment to the actual orientation of the end effector. Such adjustments at such locations/points may be incorporated into the control scheme of subsequent inspection procedures of the same (or at least substantially similar component) to improve the positioning and orientation of the end effector.

Figure 9:
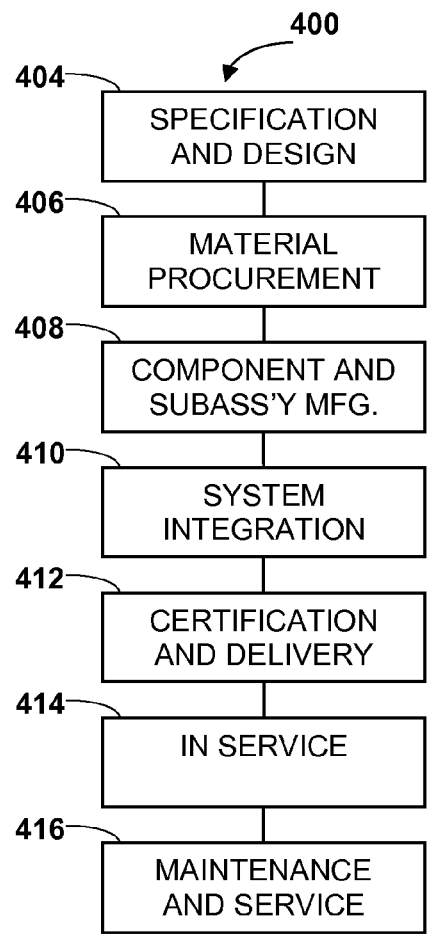
FIG. 9 is a flow diagram of aircraft production and service methodology.
Figure 10:
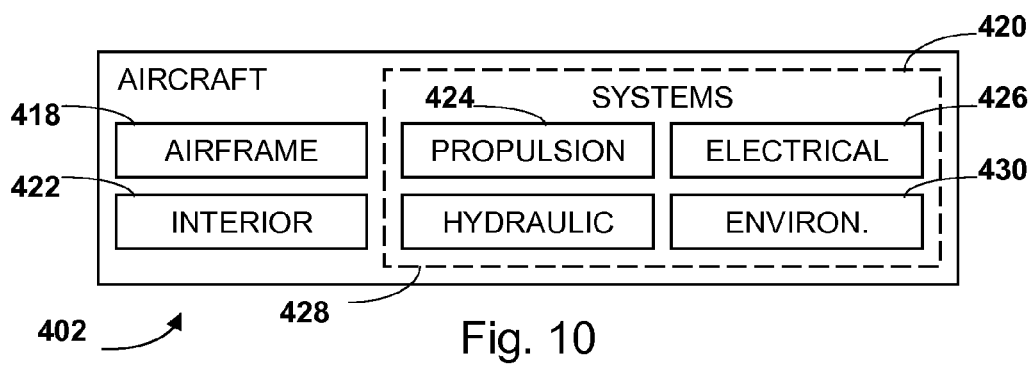
FIG. 10 is a block diagram of an aircraft.

Referring more particularly to the drawings, embodiments of the disclosure may be described in the context of an aircraft manufacturing and service method 400 as shown in FIG. 9 and an aircraft 402 as shown in FIG. 10. During pre-production, exemplary method 400 may include specification and design 404 of the aircraft 402 and material procurement 406. During production, component and subassembly manufacturing 408 and system integration 410 of the aircraft 402 takes place. Thereafter, the aircraft 402 may go through certification and delivery 412 in order to be placed in service 414. While in service by a customer, the aircraft 402 is scheduled for routine maintenance and service 416 (which may also include modification, reconfiguration, refurbishment, and so on).

Each of the processes of method 400 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 10, the aircraft 402 produced by exemplary method 400 may include an airframe 418 with a plurality of systems 420 and an interior 422. Examples of high-level systems 420 include one or more of a propulsion system 424, an electrical system 426, a hydraulic system 426, and an environmental system 430. Any number of other systems may be included. Although an aerospace example is shown, the principles of the invention may be applied to other industries, such as the automotive industry.

Apparatus and methods embodied herein may be employed during any one or more of the stages of the production and service method 400. For example, components or subassemblies corresponding to production process 408 may be fabricated or manufactured in a manner similar to components or subassemblies produced while the aircraft 402 is in service. Also, one or more apparatus embodiments, method embodiments, or a combination thereof may be utilized during the production stages 408 and 410, for example, by substantially expediting assembly of or reducing the cost of an aircraft 402. Similarly, one or more of apparatus embodiments, method embodiments, or a combination thereof may be utilized to detect crack formations while the aircraft 402 is in service, for example and without limitation, to maintenance and service 416.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As will be appreciated by one skilled in the art, aspects of the present disclosure can be embodied as a system, method, and/or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wire-line, optical fiber, Radio Frequency (RF), or the like, or any suitable combination of the foregoing.

In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor.

Program code for carrying out operations for aspects of the present disclosure may be written in any combination of one or more programming languages, including an object oriented programming language such as Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program product may be stored on a shared file system accessible from one or more servers. The computer program product may be executed via transactions that contain data and server processing requests that use Central Processor Unit (CPU) units on the accessed server. CPU units may be units of time such as minutes, seconds, hours on the central processor of the server. Additionally the accessed server may make requests of other servers that require CPU units. CPU units are an example that represents but one measurement of use. Other measurements of use include but are not limited to network bandwidth, memory usage, storage usage, packet transfers, complete transactions, etc.

Aspects of the embodiments may be described above with reference to schematic flowchart diagrams and/or schematic block diagrams of methods, apparatuses, systems, and computer program products according to embodiments of the disclosure. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present disclosure. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A system for inspecting a component, comprising:
   an ultrasonic inspection probe comprising a component surface interface;
   a robotic device comprising an end effector coupled to the ultrasonic inspection probe by an articulation subsystem comprising a two-axis gimbal structure arranged to passively absorb pitch and roll movement of the ultrasonic inspection probe, wherein the robotic device is automatably controllable to move the ultrasonic inspection probe across a surface of the component;
   an angle sensor subsystem coupled to the two-axis gimbal structure, wherein the angle sensor subsystem is configured to operably detect an actual orientation of the end effector relative to a presently inspected portion of the surface of the component; and
   a controller configured to receive orientation data from the angle sensor subsystem based on the actual orientation of the end effector, compare the actual orientation to a desired orientation, and control the robotic device to adjust the actual orientation of the end effector to be in the desired orientation.

2. The system of claim 1, wherein the desired orientation comprises a longitudinal axis of the end effector perpendicular to the presently inspected portion of the surface of the component.

3. The system of claim 1, wherein the articulation subsystem is coupled between the inspection probe and the end effector, and further wherein the articulation subsystem is configured to operably maintain the component surface interface properly engaged with the presently inspected portion of the surface of the component.

4. The system of claim 3, wherein the two-axis gimbal structure is coupled between the ultrasonic inspection probe and the end effector, and further wherein the two-axis gimbal structure, being configured to passively absorb pitch and roll movement of the ultrasonic inspection probe maintains the component surface interface substantially parallel to the presently inspected portion of the surface of the component.

5. The system of claim 4, wherein the articulation subsystem further comprises a pneumatic actuator coupled between the two-axis gimbal structure and the end effector, wherein the pneumatic actuator is configured to passively absorb movement of the ultrasonic inspection probe, via the two-axis gimbal structure, along an axis substantially perpendicular to the presently inspected portion of the surface of the component.

6. The system of claim 4, wherein the angle sensor subsystem comprises a plurality of transducers coupled to the two-axis gimbal structure.

7. The system of claim 6, wherein the plurality of transducers comprises a rotary variable differential transformer (RVDT) coupled to each axis of the two-axis gimbal structure.

8. The system of claim 1, wherein the ultrasonic inspection probe comprises:
   a housing;
   an ultrasonic array coupled to the housing;
   a component surface interface of the housing, the component surface interface comprising a liquid couplant port, an engagement lip engageable with a surface of the component, and at least one vacuum port, wherein the engagement lip circumferentially circumscribes the liquid couplant port and the at least one vacuum port circumferentially circumscribes the engagement lip, wherein the at least one vacuum port is fluidly coupleable with a vacuum source;
   a liquid couplant chamber disposed between the ultrasonic array and the liquid couplant port of the component surface interface, wherein the liquid couplant chamber is in fluid communication with the liquid couplant port and the liquid couplant chamber is fluidly coupleable with a liquid couplant supply; and
   the articulation subsystem coupled to the housing and configured to operably maintain the engagement lip of the component surface interface properly engaged with the presently inspected portion of the surface of the component.

9. An apparatus for inspecting a component, comprising:
   a housing;
   an ultrasonic array coupled to the housing;
   a component surface interface of the housing, the component surface interface comprising a liquid couplant port, an engagement lip engageable with a surface of the component, and at least one vacuum port, wherein the engagement lip has an annular shape and circumferentially circumscribes the liquid couplant port and the at least one vacuum port has an annular shape and circumferentially circumscribes the engagement lip, wherein the at least one vacuum port is fluidly coupleable with a vacuum source;
   a liquid couplant chamber disposed between the ultrasonic array and the liquid couplant port of the component surface interface, wherein the liquid couplant chamber is in fluid communication with the liquid couplant port and the liquid couplant chamber is fluidly coupleable with a liquid couplant supply; and
   an end effector of a robotic device, coupled to an articulation subsystem, wherein the robotic device is automatably controllable to move the apparatus across the surface of the component;
   wherein the articulation subsystem comprises a two-axis gimbal structure coupled between the housing and the end effector, and is configured to operably maintain the component surface interface properly engaged with a presently inspected portion of the surface of the component.

10. The apparatus of claim 9, further comprising a central axis extending from the ultrasonic array and through the liquid couplant chamber and liquid couplant port, wherein the articulation subsystem is configured to operably maintain the central axis substantially perpendicular to the presently inspected portion of the surface of the component.

11. The apparatus of claim 9, wherein the engagement lip of the component surface interface is protruded relative to the at least one vacuum port so as to be positionable closer to the surface of the component relative to the at least one vacuum port.

12. The apparatus of claim 9, wherein the two-axis gimbal structure is configured to passively absorb pitch and roll movement of the housing.

13. The apparatus of claim 9, wherein the articulation subsystem further comprises a pneumatic actuator coupled between the two-axis gimbal structure and the end effector, wherein the pneumatic actuator is configured to passively absorb movement of the housing, via the two-axis gimbal structure, along an axis substantially perpendicular to the presently inspected portion of the surface of the component.

14. The apparatus of claim 9, further comprising: an angle sensor subsystem coupled to the two-axis gimbal structure, wherein the angle sensor subsystem is configured to detect an actual orientation of the end effector relative to the presently inspected portion of the surface of the component; and a controller configured to receive orientation data from the angle sensor subsystem corresponding to the actual orientation of the end effector, compare the actual orientation to a desired orientation, and control the robotic device to adjust the actual orientation of the end effector to be in the desired orientation.

15. The apparatus of claim 14, wherein the desired orientation comprises a longitudinal axis of the end effector perpendicular to the presently inspected portion of the surface of the component.

16. The apparatus of claim 14, wherein the angle sensor subsystem comprises a plurality of transducers coupled to the two-axis gimbal structure.

17. The apparatus of claim 16, wherein the plurality of transducers comprises a rotary variable differential transformer (RVDT) coupled to each axis of the two-axis gimbal structure.

18. A method for inspecting a component, comprising:
robotically moving an ultrasonic inspection probe across a surface of the component to inspect structural characteristics of the component, wherein moving the ultrasonic inspection probe comprises automatably controlling a robotic device comprising an end effector to which the ultrasonic inspection probe is coupled by an articulation subsystem comprising a two-axis gimbal structure arranged to passively absorb pitch and roll movement of the ultrasonic inspection probe;
detecting an actual orientation of the end effector relative to a presently inspected portion of the surface of the component, wherein detecting the actual orientation of the end effector comprises receiving orientation data from an angle sensor subsystem that is coupled to the two-axis gimbal structure;
comparing the actual orientation to a desired orientation; and
controlling the robotic device to adjust the actual orientation of the end effector to be in the desired orientation.

19. The method of claim 18, further comprising adjusting the actual orientation of the end effector according to predetermined orientation adjustments at predetermined locations across the surface of the component from a previously performed inspection of the component.

* * * * *